United States Patent
Yamamoto (10) Patent No.: US 10,430,716 B2
(45) Date of Patent: *Oct. 1, 2019

(54) DATA DRIVEN FEATURIZATION AND MODELING

(71) Applicant: Grand Rounds, Inc., San Francisco, CA (US)

(72) Inventor: Seiji James Yamamoto, San Francisco, CA (US)

(73) Assignee: GROUND ROUNDS, INC., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/040,963

(22) Filed: Feb. 10, 2016

(65) Prior Publication Data

US 2017/0228651 A1  Aug. 10, 2017

(51) Int. Cl.
| | |
|---|---|
| *G06N 5/04* | (2006.01) |
| *G06N 20/00* | (2019.01) |
| *G16H 50/70* | (2018.01) |
| *G16H 50/20* | (2018.01) |

(52) U.S. Cl.
CPC ............. *G06N 5/04* (2013.01); *G06N 20/00* (2019.01); *G16H 50/20* (2018.01); *G16H 50/70* (2018.01)

(58) Field of Classification Search
CPC ........... G06N 5/02; G06N 5/04; G06N 99/005
USPC ......................................................... 706/46
See application file for complete search history.

(56) References Cited

U.S. PATENT DOCUMENTS

| | | | | |
|---|---|---|---|---|
| 7,480,640 | B1* | 1/2009 | Elad ...................... | G06Q 10/10 706/14 |
| 7,499,897 | B2* | 3/2009 | Pinto ...................... | G06Q 30/02 706/11 |
| 2004/0059697 | A1* | 3/2004 | Forman ................ | G06K 9/6228 706/46 |
| 2005/0234740 | A1* | 10/2005 | Krishnan .......... | G06Q 10/06398 705/2 |
| 2006/0106743 | A1* | 5/2006 | Horvitz ................ | G06N 99/005 706/21 |
| 2012/0004893 | A1* | 1/2012 | Vaidyanathan ..... | G06F 19/3437 703/11 |
| 2014/0100703 | A1* | 4/2014 | Dull ....................... | G05B 17/02 700/289 |

(Continued)

OTHER PUBLICATIONS

Pinsky M. et al., "Gleaning Knowledge from Data in the Intensive Care Unit", American Journal of Respiratory and Critical Care Medicine, vol. 190, No. 6, Sep. 15, 2014.*

*Primary Examiner* — Dave Misir
(74) *Attorney, Agent, or Firm* — Finnegan, Henderson, Farabow, Garrett & Dunner, LLP (57) ABSTRACT

Computer-implemented systems and methods are disclosed for automatically generating predictive models using data driven featurization. The systems and methods provide for obtaining data associated with a target event, annotating the data to identify a target event and establishing one or more limits on the data, censoring the data based on the annotations, determining features of the censored data, and analyzing the features to determine a predictive model. In some embodiments, the systems and methods further provide for converting the features into a binary representation and analyzing the binary representation to produce the predictive model.

18 Claims, 6 Drawing Sheets

(56) References Cited

U.S. PATENT DOCUMENTS

| | | | | |
|---|---|---|---|---|
| 2014/0358826 A1* | 12/2014 | Traupman | ............... | G06N 5/048 706/11 |
| 2015/0248613 A1* | 9/2015 | Harris | ................. | G06F 19/3443 706/46 |
| 2015/0257712 A1* | 9/2015 | Sarrafzadeh | .......... | G06F 19/345 600/301 |
| 2015/0379428 A1* | 12/2015 | Dirac | ................... | G06N 99/005 706/12 |
| 2016/0148103 A1* | 5/2016 | Sarrafzadeh | ............. | G06N 5/04 706/46 |

* cited by examiner

| | Person ID | Gender | Age | Location | Job Type |
|---|---|---|---|---|---|
| 301 | 1 | M | 54 | 20002 | Construction |
| 302 | 2 | M | 60 | 94403 | Engineering |
| 303 | 3 | F | 46 | 94301 | Service |
| 304 | 4 | F | 70 | 43081 | Management |
| 305 | 5 | M | 27 | 10001 | Accounting |
| | . | . | . | . | . |
| | . | . | . | . | . |
| | . | . | . | . | . |
| 399 | N | M | 32 | 46556 | Military |

| | 310 | 320 | 330 | 340 | 350 |

| Event ID | Person ID | Cost | Code 1 | Code 2 | Code 3 | Date |
|---|---|---|---|---|---|---|
| A | 1 | $8,000 | 409 | 10021 | R0076 | 1/1/2010 |
| B | 1 | $2,500 | 531 | 0001F | C9602 | 9/26/2012 |
| C | 1 | $100 | 461 | 47350 | A9152 | 7/27/2015 |
| D | 3 | $1,200 | 780.52 | 72345 | A9273 | 7/23/2005 |
| E | 5 | $180 | 787 | 99214 | G0009 | 3/17/2011 |
| F | 5 | $55 | 786.2 | 99213 | A4209 | 6/3/2013 |
| . | . | . | . | . | . | . |
| . | . | . | . | . | . | . |
| . | . | . | . | . | . | . |
| ZZ | N | $150 | 523 | 97154 | G0205 | 2/5/2014 |

DATA DRIVEN FEATURIZATION AND MODELING

BACKGROUND

An ever increasing amount of data and data sources are now available to researchers, analysts, organizational entities, and others. This influx of information allows for sophisticated analysis but, at the same time, presents many new challenges for sifting through the available data and data sources to locate the most relevant and useful information in predictive modeling. As the use of technology continues to increase, so, too, will the availability of new data sources and information.

Analysis of large amounts of data can provide insights into the relationship between past and future events. Predictive models, built using historical data, can be applied to current data sets in an attempt to predict future outcomes or events. To effectively predict a specific event, a model must identify specific data points or features that indicate that the target event might occur. Because of the extensive amount of available data, however, determining which specific features of the existing data are relevant poses significant challenges. Additionally, different domains can have different relevant indicators.

Moreover, a predictive model must be generic enough to effectively apply to a wide variety of future data sets and, at the same time, specific enough to provide accurate prediction. Striking the balance between high model performance and generalizability to new data is especially challenging when there are many millions or billions of features and many different types of models that need to be built.

While current predictive models can be built using analysis, research, existing publications, and discussions with domain experts, this process can be resource and time intensive. Further, while the produced model may be effective for predicting a specific event, the time and resources necessary to produce similar predictive models for many thousands of additional events is not feasible. Currently, there is a need for accurate and efficient generation of predictive data models that can apply across domains and indicate what specific features of existing data most effectively predict a future event.

BRIEF DESCRIPTION OF THE DRAWINGS

Reference will now be made to the accompanying drawings showing example embodiments of this disclosure. In the drawings.

DETAILED DESCRIPTION

Reference will now be made in detail to the exemplary embodiments implemented according to the present disclosure, the examples of which are illustrated in the accompanying drawings. Wherever possible, the same reference numbers will be used throughout the drawings to refer to the same or like parts.

The embodiments described herein provide technologies and techniques for evaluating vast amounts and types of data to allow for efficient creation of predictive models. These technologies can extract information from large and varied data sets, transform the data into a consistent format, analyze the data to produce specific features associated with an entity or individual across the data, analyze the features to determine which specific features are most indicative of an event or outcome and how many of those features are reliable for accurate prediction on future data, and analyze the generated models to ensure accuracy, reliability, and better generation of future or additional predictive models.

The embodiments disclosed further include technologies for obtaining data associated with a target event, annotating the data to identify a target event and establishing one or more limits on the data, censoring the data based on the annotations, determining features of the censored data, and analyzing the features to determine a predictive model. In some embodiments, the systems and methods further provide for converting the features into a binary representation and analyzing the binary representation to produce the predictive model.

The technologies described can convert feature information into a binary representation utilizing techniques such as quantile binning. Moreover, the technologies can analyze the feature data, in both binary and non-binary form, using statistical analysis techniques such as chi-square ($\chi^2$) testing and association rule learning. Moreover, the described embodiments can utilize feedback from application of the predictive model to additional data as well as feedback from domain experts.

The embodiments described herein can apply to many fields. Descriptions and applications related to specific domains do not preclude the application of the described embodiments to other technologies of fields.

Figure 1:
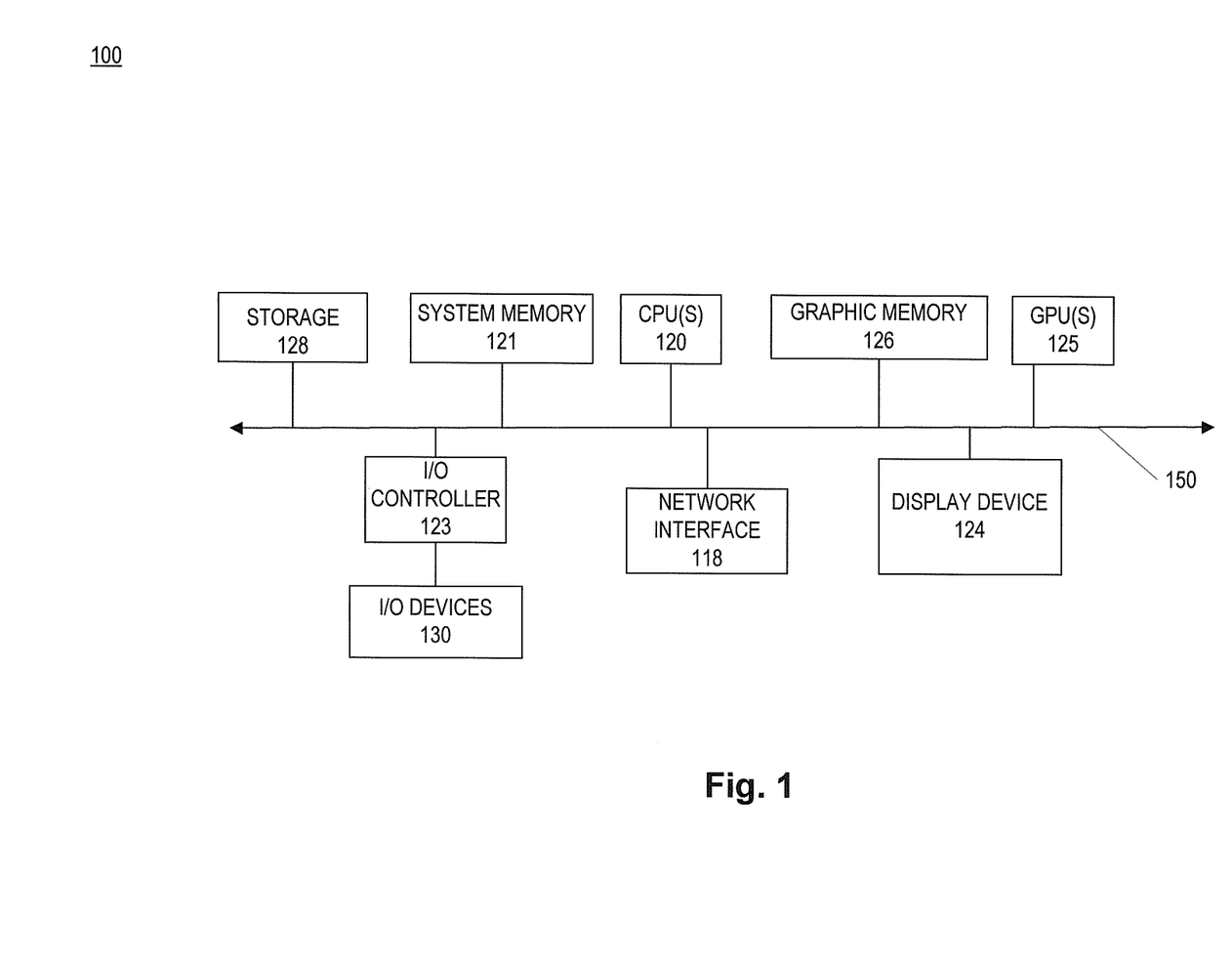
FIG. 1 is a block diagram of an exemplary computing device, consistent with embodiments of the present disclosure.

FIG. 1 is a block diagram of an exemplary computing device 100, consistent with embodiments of the present disclosure. In some embodiments, computing device 100 can be a server providing the functionality described herein. Further, computing device 100 can be a second device providing the functionality described herein or receiving information from a server to provide at least some of that information for display. Moreover, computing device 100 can be an additional device or devices that store and/or provide data consistent with embodiments of the present disclosure.

Computing device 100 can include one or more central processing units (CPUs) 120 and system memory 121. Computing device 100 can also include one or more graphics processing units (GPUs) 125 and graphic memory 126. CPUs 120 can be single or multiple microprocessors, field-programmable gate arrays, or digital signal processors capable of executing sets of instructions stored in a memory (e.g., system memory 121), a cache, or a register. CPUs 120 can contain one or more registers for storing variable types of data including, inter alia, data, instructions, floating point values, conditional values, memory addresses for locations in memory (e.g., system memory 121 or graphic memory 126), pointers and counters. CPU registers can include special purpose registers used to store data associated with executing instructions such as an instruction pointer, instruction counter, and/or memory stack pointer. System memory 121 can include a tangible and/or non-transitory computer-readable medium, such as a flexible disk, a hard disk, a compact disk read-only memory (CD-ROM), magneto-optical (MO) drive, digital versatile disk random-access memory (DVD-RAM), a solid-state disk (SSD), a flash drive and/or flash memory, processor cache, memory register, or a semiconductor memory. System memory 121 can be one or more memory chips capable of storing data and allowing direct access by CPUs 120. System memory 121 can be any type of random access memory (RAM), or other available memory chip capable of operating as described herein.

CPUs 120 can communicate with system memory 121 via a system interface 150, sometimes referred to as a bus. GPUs 125 can be any type of specialized circuitry that can manipulate and alter memory (e.g., graphic memory 126) to provide and/or accelerate the creation of images. GPUs 125 can store images in a frame buffer for output to a display device such as display device 124. GPUs 125 can have a highly parallel structure optimized for processing large, parallel blocks of graphical data more efficiently than general purpose CPUs 120. Furthermore, the functionality of GPUs 125 can be included in a chipset of a special purpose processing unit or a co-processor.

CPUs 120 can execute programming instructions stored in system memory 121 or other memory, operate on data stored in memory (e.g., system memory 121) and communicate with GPUs 125 through the system interface 150, which bridges communication between the various components of computing device 100. In some embodiments, CPUs 120, GPUs 125, system interface 150, or any combination thereof, are integrated into a single chipset or processing unit. GPUs 125 can execute sets of instructions stored in memory (e.g., system memory 121), to manipulate graphical data stored in system memory 121 or graphic memory 126. For example, CPUs 120 can provide instructions to GPUs 125, and GPUs 125 can process the instructions to render graphics data stored in the graphic memory 126. Graphic memory 126 can be any memory space accessible by GPUs 125, including local memory, system memory, on-chip memories, and hard disk. GPUs 125 can enable displaying of graphical data stored in graphic memory 126 on display device 124.

Computing device 100 can include display device 124 and input/output (I/O) devices 130 (e.g., a keyboard, a mouse, or a pointing device) connected to I/O controller 123. I/O controller 123 can communicate with the other components of computing device 100 via system interface 150. It is appreciated that CPUs 120 can also communicate with system memory 121 and other devices in manners other than through system interface 150, such as through serial communication or direct point-to-point communication. Similarly, GPUs 125 can communicate with graphic memory 126 and other devices in ways other than system interface 150. In addition to receiving input, CPUs 120 can provide output via I/O devices 130 (e.g., through a printer, speakers, or other output devices).

Furthermore, computing device 100 can include a network interface 118 to interface to a LAN, WAN, MAN, or the Internet through a variety of connections including, but not limited to, standard telephone lines, LAN or WAN links (e.g., 802.11, T1, T3, 56 kb, X.25), broadband connections (e.g., ISDN, Frame Relay, ATM), wireless connections, or some combination of any or all of the above. Network interface 118 can comprise a built-in network adapter, network interface card, PCMCIA network card, card bus network adapter, wireless network adapter, USB network adapter, modem or any other device suitable for interfacing computing device 100 to any type of network capable of communication and performing the operations described herein.

Figure 2:
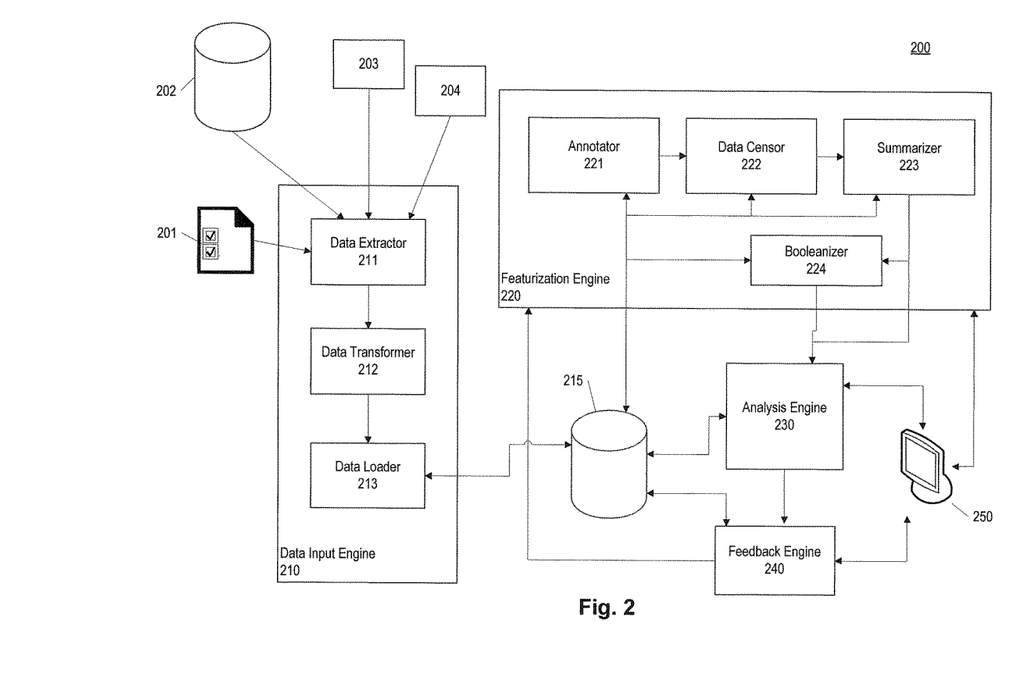
FIG. 2 is a block diagram of an exemplary system for data driven featurization, consistent with embodiments of the present disclosure.

FIG. 2 is a block diagram representing exemplary system 200 for data driven featurization consistent with embodiments of the present disclosure. System 200 can include data input engine 210 that can further include data extractor 211, data transformer 212, and data loader 213. Data input engine 210 can process data from data sources 201-204. Data input engine 210 can be implemented using computing device 100 from FIG. 1. For example, data from data sources 201-204 can be obtained through I/O devices 130 and/or network interface 118. Further, the data can be stored during processing in a suitable storage such as storage 128 and/or system memory 121. Data input engine 210 can also interact with data storage 215. Data storage 215 can further be implemented on a computing device such as computing device 100 that stores data in storage 128 and/or system memory 121 as shown in FIG. 1. System 200 can include featurization engine 220. Featurization engine 220 can comprise annotator 221, data censor 222, summarizer 223, and booleanizer 224. System 200 can also include analysis engine 230 and feedback engine 240. Similarly to data input engine 210, featurization engine 220 can be implemented on a computing device such as computing device 100 from FIG. 1. Similarly, featurization engine 220 can utilize storage 128 and/or system memory 121 for storing data and can utilize I/O device 130 or network interface 118 for transmitting and/or receiving data. Each of data input engine 210, data extractor 211, data transformer 212, data loader 213, featurization engine 220, annotator 221, data censor 222, summarizer 223, booleanizer 224, analysis engine 230, and feedback engine 240 can be a module, which is a packaged functional hardware unit designed for use with other components or a part of a program that performs a particular function of related functions. Each of these modules can be implemented using computing device 100 of FIG. 1. Each of these components is described in more detail below. In some embodiments, the functionality of system 200 can be split across multiple computing devices (e.g., multiple devices similar to computing device 100) to allow for distributed processing of the data. In these embodiments the different components can communicate over I/O device 130 or network interface 118.

System 200 can be related to many different domains or fields of use. Descriptions of embodiments related to specific domains, such as healthcare, is not intended to limit the disclosed embodiments to a those specific domains, and embodiments consistent with the present disclosure can apply to any domain that utilizes predictive modeling based on available data.

Data input engine 210 is a module that can retrieve data from a variety of data sources (e.g., data source 201, 202, 203, and 204) and process the data so that it can be used with the remainder of system 200. Data input engine 210 can further include data extractor 211, data transformer 212, and data loader 213.

Data extractor 211 retrieves data from data sources 201, 202, 203, and 204. Each of these data sources can represent a different type of data source. For example, data source 201 can be a database. Data source 202 can represent structured data. Data sources 203 and 204 can be flat files. Further, data sources 201-204 can contain overlapping or completely disparate data sets. In some embodiments, data source 201 can contain individual information while data sources 202, 203, and 204 contain various insurance claim and medical treatment data. For example, data source 201 can contain data structure 300 of FIG. 3 and data source 202 can contain data structure 400 of FIG. 4. Data extractor 211 can interact with the various data sources, retrieve the relevant data, and provide that data to data transformer 212.

Data transformer 212 can receive data from data extractor 211 and process the data into standard formats. In some embodiments, data transformer 212 can normalize data such as dates. For example data source 201 can store dates in day-month-year format while data source 202 can store dates in year-month-day format. In this example, data transformer 212 can modify the data provided through data extractor 211 into a consistent date format. Accordingly, data transformer 212 can effectively clean the data provided through data extractor 211 so that all of the data, although originating from a variety of sources, has a consistent format.

Moreover, data transformer 212 can extract additional data points from the data. For example, data transformer can process a date in year-month-day format by extracting separate data fields for the year, the month, and the day. Data transformer can also perform other linear and non-linear transformations and extractions on categorical and numerical data such as normalization and demeaning. Data transformer 212 can provide the transformed and/or extracted data to data loader 213.

Data loader 213 can receive the normalized data from data transformer 212. Data loader 213 can merge the data into varying formats depending on the specific requirements of system 200 and store the data in an appropriate storage mechanism such as data storage 215. In some embodiments, data storage 215 can be data storage for a distributed data processing system (e.g., Hadoop Distributed File System, Google File System, ClusterFS, and/or OneFS). In some embodiments, data storage 215 can be a relational database (described in more detail below). Depending on the specific embodiment, data loader 213 can optimize the data for storing and processing in data storage 215. In some embodiments, data structures 300 and 400 from FIGS. 3 and 4 (or versions thereof) can be stored by data loader 213 in data storage 215.

Featurization engine 220 can process the data prepared by data input engine 210 and stored in data storage 215. Featurization engine 220 can include annotator 221, data censor 222, summarizer 223, and booleanizer 224. Featurization can retrieve data from data storage 215 that has been prepared by date input engine 210. For example, data structures 200 and 300 of FIGS. 2 and 3 can be suitable inputs to featurization engine 220.

Figure 3:
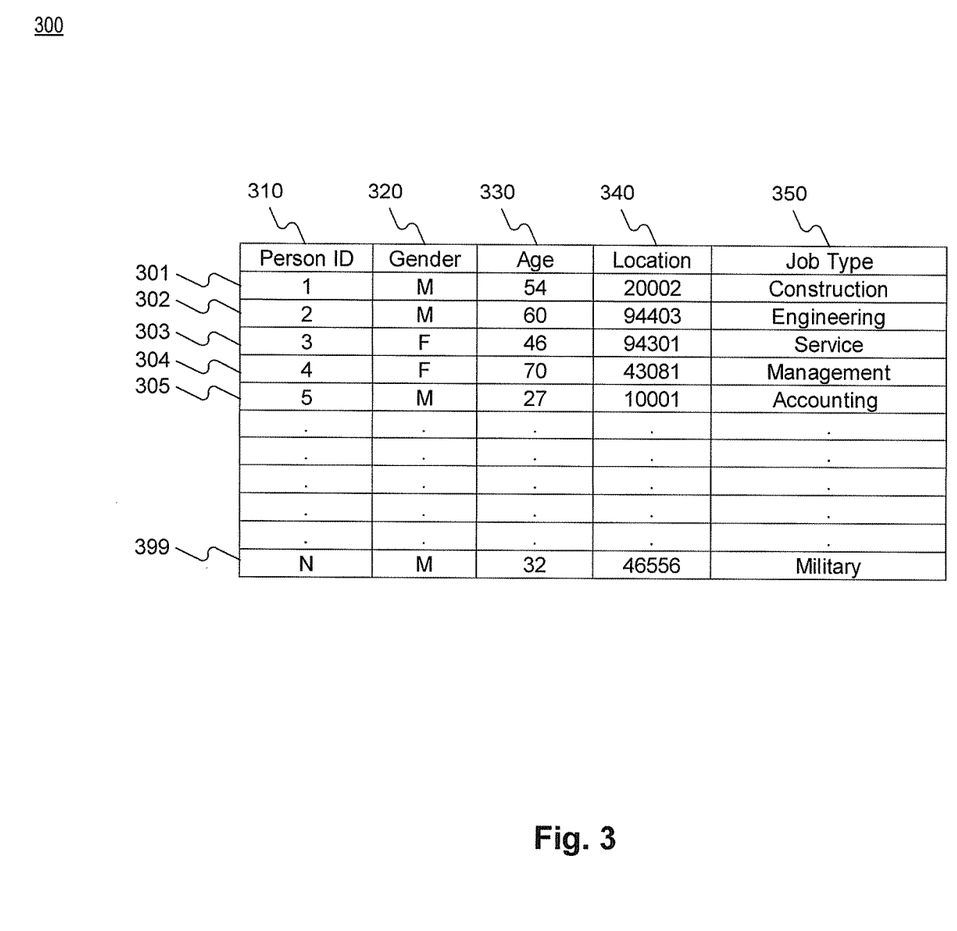
FIG. 3 is an exemplary data structure consistent with embodiments of the present disclosure.

As shown in FIG. 3, data structure 300 is an exemplary data structure, consistent with embodiments of the present disclosure. Data structure 300 can store data records associated with individuals or entities. Data structure 300 can, for example, be a database, a flat file, data stored in memory (e.g., system memory 121), and/or data stored in any other suitable storage mechanism (e.g., storage 128).

In some embodiments, data structure 300 can be a Relational Database Management System (RDBMS) (e.g., Oracle Database, Microsoft SQL Server, MySQL, PostgreSQL, and/or IBM DB2). An RDBMS can be designed to efficiently return data for an entire row, or record, in as few operations as possible. An RDBMS can store data by serializing each row of data of data structure 300. For example, in an RDBMS, data associated with record 301 of FIG. 3 can be stored serially such that data associated with all categories of record 301 can be accessed in one operation. Moreover, an RDBMS can efficiently allow access of related records stored in disparate tables. For example, in an RDBMS, data structure 300 of FIG. 3 and data structure 400 (described in more detail below) of FIG. 4 can be linked by a referential column. In this example, person ID 420 of data structure 400 can directly relate to person ID 310 of data structure 300. An RDBMS can allow for the efficient retrieval of all records in data structure 400 associated with a record of data structure 300 based on a common value for the respective person ID fields (e.g., person ID 420 of data structure 400 and person ID 310 of data structure 300).

In some embodiments, data structure 300 of FIG. 3 can be a non-relational database system (NRDBMS) (e.g., XML, Cassandra, CouchDB, MongoDB, Oracle NoSQL Database, FoundationDB, and/or Redis). A non-relational database system can store data using a variety of data structures such as, among others, a key-value store, a document store, a graph, and a tuple store. For example, a non-relational database using a document store could combine all of the data associated with a particular person ID (e.g, person ID 310 of data structure 300 and person ID 420 of data structure 400 in FIG. 4) into a single document encoded using XML. In this example, the XML document would include the information stored in record 310 of data structure 300 and records 401-403 of data structure 400 based on all of these records sharing the same person ID value.

Data structure 300 of FIG. 3 can store information related to individuals. Data structure 300 can include data records 301-305 representing individuals in addition to countless additional records up to record 399. Data structure 300 can contain many millions or billions of records of data and is limited only by the physical constraints of the system upon which the data structure exists.

Data structure 300 can include categories of data. For example data structure 300 can include categories person ID 310, gender 320, age 330, location 340, and job type 350. Data associated with data records 301-305 can be stored under each of these categories. For example, an individual represented by data record 301 has a person ID of "1," is male as represented by an "M" under gender 320, is 54 as listed under age 330, lives in zip code "20002" as represented under location 340, and works in construction as indicated under job type 350.

In some embodiments, data structure 300 can contain more or fewer categories for each data record. For example, data structure 300 can include additional categories of data such as household income, height, weight, eye color, hair color, race, education, or any other category of data associated with an individual. Moreover, depending on the circumstances data structure 300 can contain domain specific data. For example, in a healthcare context, data structure 300 can include insurance provider information, family medical history information, immunization information, or other healthcare specific data. Accordingly data structure 300 is not limited to only those categories shown in FIG. 3.

In some embodiments, data structure 300 contains categories that store similar data. For example, data structure 300 can include location 340 that represents a home address zip code, while an additional "location" category (not shown) can be used to store a business zip code.

Additionally, data structure 300 can include combination categories. For example, instead of only using location 340 to represent location information, data structure 300, in some embodiments, includes categories for, among others, street address, state, city, and/or country. This data can be stored under one category or separate categories that, together, represent a location.

Moreover, location 340 can store different types of data. In some embodiments, location 340 is a zip code. In other embodiments, location 340 is a combination category as previously described. Location 340 can further include, geospatial coordinates, map coordinates, or any other data type that indicates location.

Similarly to location 340, other categories, such as age 330 and job type 350, can include data in a variety of formats. For example, age 330 can be represented in years, in years and months, in days, or by a date of birth. Additionally, job type can be a specific job title, job classification, and/or industry.

In some embodiments, data stored under a category can be a reference into another data set or data structure as is common in relational data sets. For example, job type 350 can contain an identifier that references a description stored in a separate data set or lookup table instead of containing text or another data type.

Figure 4:
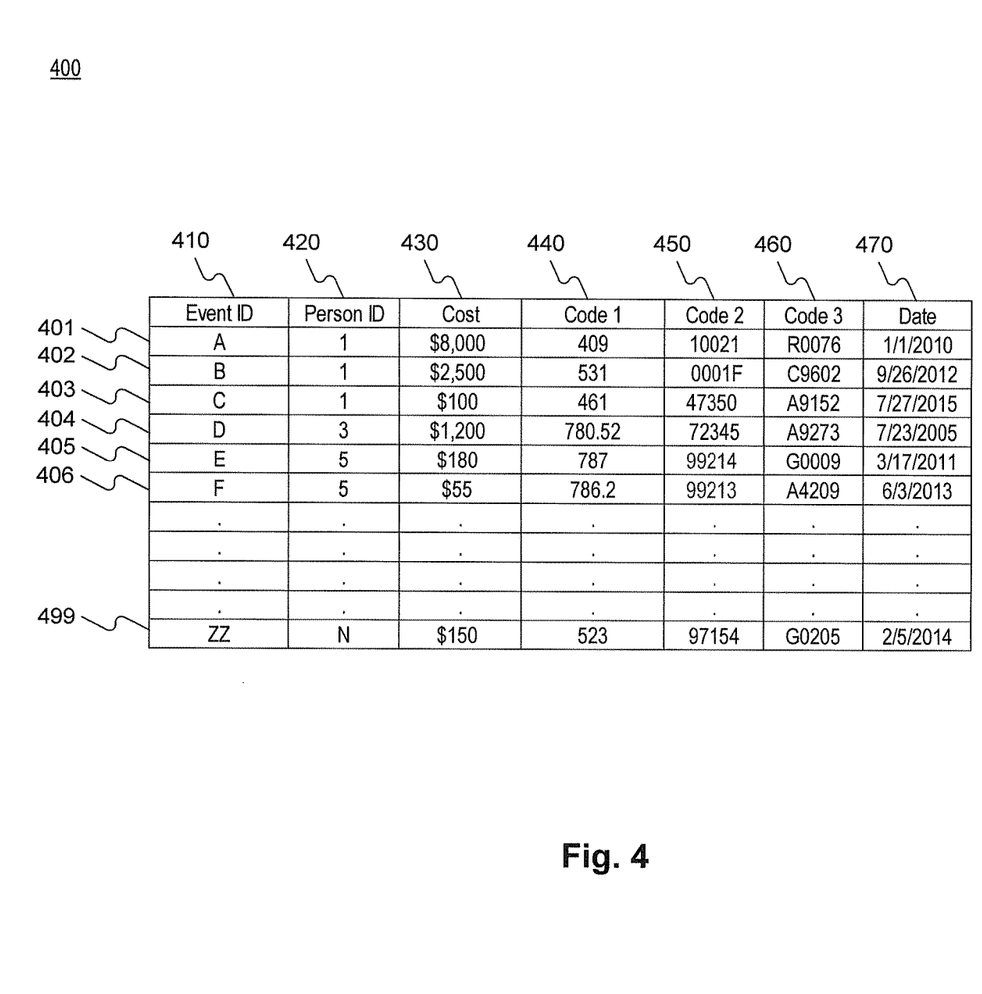
FIG. 4 is an exemplary data structure consistent with embodiments of the present disclosure.

Additionally, as shown in FIG. 4, data structure 400 is an exemplary data structure, consistent with embodiments of the present disclosure. Data structure 400 can store data records associated with events that are further associated with specific individuals. Similarly to data structure 300 described in FIG. 3, data structure 400 can, for example, be a database, a flat file, data stored in memory (e.g., system memory 121 of computing device 100 from FIG. 1), an RDBMS, an NRDBMS, and/or data stored in any other suitable storage mechanism (e.g., storage 128 of computing device 100 from FIG. 1). Moreover, data structure 400 can be implemented or stored computing device similar to computing device 100 described in FIG. 1.

Data structure 400 can store information related to events. Data structure 400 can include data records 401-406 representing data associated with specific events in addition to countless additional records up to record 499. Data structure 400 can contain many millions or billions of records of data and is limited only by the physical constraints of the system upon which the data structure exists.

Data structure 400 can include categories of data. For example, data structure 400 can include the categories event ID 410, person ID 420, cost 430, code 1 440, code 2 450, code 3 460 and date 470. Data associated with data records 401-406 can be stored in each respective row of data structure 400 within one of these categories. For example, an event represented by data record 401 is associated with a person ID 310 of "1," has a cost 430 of "$8000," has values of "409," "10021," and "R0076," for code 1 440, code 2 450, and code 3 460, respectively, and a date 470 of Jan. 1, 3010.

Moreover, data structure 400 can include multiple data records associated with the same individual. For example, data records 401-403 all have a value of 1 for person ID 420. These values can refer to a person ID number stored in a separate data set. For example, person ID 420 can refer to person ID 310 of data structure 300 described in FIG. 3. In this example, data records 401-403 of data structure 400 can be associated with data record 301 of data structure 300. Moreover, data record 404 of data structure 400 can be associated with data record 303 of data structure 300 and data records 405-406 of data structure 400 can be associated with data record 305 of data structure 300 based on the values in person ID 420 and person ID 310 of data structure 300 in FIG. 3.

In some embodiments, the data records in data structure 400 are all related to the same type of event or a specific domain. For example, data structure 400 can contain data records related to medical insurance claims. In these embodiments, data structure 400 includes additional categories that are specific to these types of events or domains, such as categories for deductibles and/or physician identifiers. Moreover, in these embodiments, existing categories may contain information related to the domain of the data. For example, in embodiments where data structure 400 includes health insurance claim data, code 1 440, code 2 450, and code 3 460 can represent International Statistical Classification of Diseases and Related Health Problems (ICD) codes, Current Procedural Terminology (CPT) codes, and Healthcare Common Procedure Coding System (HCPCS) codes respectively. In a different domain, code 1 440, code 2 450, and code 3 460 can represent different identifying information for the events represented in data structure 400.

Similarly to data structure 300, data structure 400 can include more or fewer categories for each data record depending on the domain and the source of the data record. Additionally, as described in relation to data structure 300, some categories of data structure 400 can store data in different formats that represent the same concept, such as a date or cost. For example, Date 470 can contain only a month and year, or can contain month, day, and year. In a similar example, cost can contain values in terms of United States Dollars or in terms of other currencies.

Referring back to FIG. 2, featurization engine 220 can process the data from data storage 215. This data can be stored using data structures such as data structures 300 and 400 shown in FIGS. 3 and 4 respectively. Feauturization engine 220 can convert the data into features that can then be used for additional analysis. A feature can be data that is representative of other data. Features can be determined based on the domain, data type of a category, or many other factors associated with data stored in a data structure. Additionally, a feature can represent information about multiple data records in a data set or information about a single category in a data record. Moreover, multiple features can be produced to represent the same data. Different types of features are described in more detail below.

As previously stated, a feature can be based on the data type stored for a category. A category that stores real numbers, for example, can be represented by a feature generated using functions such as minimum, maximum, average, or mean across multiple data sets. For example, a feature representing the maximum cost paid by an individual for a medical procedure can be based on the cost 430 category of data structure 400 in FIG. 4. In this example, data records 401-403 represent medical procedures for the same individual. A feature representing the maximum cost paid by that individual for a particular procedure or claim can be calculated by comparing the cost values of "$8000," "$2500," and "$100" stored in data records 401-403 and determining that "$8000" is the maximum value. This type of feature can be determined for only those records pertaining to the same individual or can be determined across a data set containing multiple individuals.

One set of data points can produce multiple features related to that data. For example, in addition to calculating the maximum cost for data records 401-403 of FIG. 4, features representing the average cost, minimum cost, mean cost, or cost distribution can also be determined from the same cost category of data records 401-403. In the case of a distribution multiple features can be generated that represent the different aspects of the distribution. For example, the distribution of the cost stored in data records 401-403 can result in features that describe the skew, kurtosis, entropy among other distribution related measurements of the cost data.

In addition to features associated with real numbers features can be based on categorizations. Categorizations can include a count of data points, specific data indicators, most frequent types of data points, or similar features. In some embodiments, in relation to healthcare data, categories can include the most expensive claim, the count of claims, particular claims known to be indicators of a specific condition, for example, a heart attack, a specific category of ICD or CPT codes, the most frequent code in the claims data, or many additional characteristics of the claims data. Each of these categories can be established as a feature.

Moreover, features can be established based on dates. In some embodiment related to healthcare and claims data, features can include the duration of certain types of claims or treatments, the onset date of a particular type of claim, or similar date data.

Features can also be based on data not directly included in the data records. In a healthcare context, for example, code 1 440, code 2 450, and code 3 460 can represent specific codes, such as ICD, CPT, or HCPCS codes that represent specific treatments. These codes can be part of a larger hierarchical system. For example, a code that represents the treatment of high insulin levels may implicitly indicate treatment for diabetes although only the code for high insulin is included in the data record. Because of the hierarchical nature of the coding system, featurization engine 220 can determine that a claim for high insulin includes both a feature for the treatment of high insulin as well as a feature representing the treatment of diabetes. In another example, data records can contain a reference, such as a National Provider Identifier (NPI), that identifies a provider. In this example, the provider information can be joined with the data records providing additional data and information for determining features. This sort of external data can be stored in, for example, data storage 215 of FIG. 2 and available to featurization engine 220 as well as the other components of system 200. These examples and descriptions of features are not exhaustive. Features can be any data descriptive of the data stored in a record. Referring back to FIG. 2, The process by which features are determined and used by featurization engine 220 is described in more detail.

Featurization engine 220 can contain annotator 221. Annotator 221 can provide context to the data structures from data storage 215. In particular, annotator 221 can establish a particular event in the data as the target event. This target event can be predetermined and provided to annotator 221. In some embodiments, the target event can be based on the predictive model being produced. For example, data showing the occurrence of a heart attack can be used as the target event for a model intended to predict heart attacks. In some embodiments, annotator 221 identifies multiple events that serve as a target event. For example when predicting a heart attack, different codes or identifiers can be used to indicate a heart attack, cardiac arrest, or other cardiac events that are related. Depending on the necessary specificity of the predictive model, annotator 221 can determine which events are closely related and represent the same target for the predictive model.

Annotator 221 can further determine which additional data records are associated with the target event and should be used in the predictive model. For example, claim data for an individual related to chest pain, shortness of breath, or other symptoms and treatments related to cardiac events can be associated with the occurrence of a heart attack. In this example, Annotator 221, can determine that claims for that same individual related to treatment of a broken finger is irrelevant. In some embodiments, annotator 221 includes seemingly unrelated data as further processing can reveal that seemingly unrelated conditions can have predictive value that can be revealed through analysis consistent with embodiments of the present disclosure. In order to determine these types of unpredictable relationships, annotator 221 can receive information from feedback engine 240 (described in more detail below) as a result of other predictive models that have been generated by system 200. For example, a generated model can predict that certain types of eye symptoms are indicative of certain types of spinal conditions, such as Ankylosing Spondylitis. Although not intuitive, this relationship can include important predictive value. Based on that previously generated model, annotator 221 can receive instructions not to disregard eye conditions when attempting to generate predictive models related to spinal conditions.

In addition to establishing a specific target event, annotator 221 can further contextualize the data by establishing a censor date. Annotator 221 can establish a date based on the identified target event after which data should be ignored. For example, after annotator 221 determines that specific claims data is related to a heart attack, annotator 221 can establish a censor date as of the time of the heart attack. Because claims data following the heart attack is unlikely to have value for predicting the heart attack, establishing a censor date can help eliminate data that could otherwise skew the predictive analysis. In some embodiments, censor dates are specific to each individual represented in the data based on the date and/or time of the target event. Moreover, similar to a censor date, annotator 221 can establish beginning and end dates outside of which data should be ignored. Annotator 221 can base the range of dates that should be considered by featurization engine 220 on the type of the target event identified. In some embodiments, all claim data before a target event will be relevant and there will be no beginning date. Moreover, in some embodiments, claims data or other data after the target event can be included in the analyzed data. Furthermore, the date range of relevant data can be specific to each individual based on the particular target event identified for each specific individual.

As an example, and in reference to data structure 400 in FIG. 4, annotator 221 can analyze claim data related to individual "1" and determine that claim data record 402 represents the target event. In this example, annotator 221 can establish "Sep. 26, 2012" as the target date. Further, in this example, annotator 221 can establish a beginning data as any claim data before Sep. 26, 2012 and an ending data as of the target event on Sep. 26, 2012. It is appreciated that annotator 221 is not limited to identifying dates. Depending on the target event identified, annotator 221 can establish limits on claims to be considered based on other characteristics. For example, in reference to data structure 400, annotator 221 can establish a maximum or minimum cost, a specific code range, or other criteria required for inclusion in further analysis.

After annotator 221 processes and identifies relevant limits on the data, data censor 222 can filter out data that does not meet the established criteria. For example, when evaluating claims data, data censor 222 can remove all claims data that has a date after the target events date or ending date or all claims data that has a date prior to the beginning date. Data censor 222 can remove all data outside of the criteria established by annotator 221 in order to improve the accuracy of the subsequent analysis.

Censoring data can be an important step in the process that focuses the analysis on relevant data sets and eliminates data that may skew the analysis. For example, if system 200 is attempting to establish a predictive model for individuals who are at risk for a heart attack by analyzing existing data, data censor can remove all claims related to the heart attack itself and subsequent treatment. By doing this, data censor 222 can ensure that the other components of featurization engine 220 and subsequent analysis does not rely on the actual occurrence of a heart attack as a feature that is predictive of a heart attack. Removal of this type of data can be helpful because the predictive model is built using past data that will include the events the model is attempting to predict. Censoring the data can be important as it helps to avoid overfitting and look-ahead bias.

After the data has been censored, summarizer 223 can analyze the remaining data structures and data to produce features for the data set. As previously described, features can be based on the specific type of data under consideration and many features can be produced from a single data point or set of data points Summarizer 223 can further consider data points occurring across multiple data records for an individual, or can consider data points related to multiple individuals. As an example, when analyzing insurance claims data, summarizer 223 can consider all remaining claims for a particular individual or can consider only individual claims dependent on the feature being produced.

In some embodiments, summarizer 223 can accept configuration settings and/or a configuration object (collectively, configuration settings) that defines the types of aggregations and/or features to extract from the data sets. Summarizer 223 can include featurizations by default based on the various data types of the data and/or can include featurizations explicitly defined by the configuration settings. The configurations included in the configuration settings can be defined by a user of system 200 or can be based on the specific domain of the data being analyzed. For example, configuration settings for a healthcare domain can include settings for generating features based on the hierarchical coding systems described above. Moreover, in a healthcare domain, configuration settings can include settings for analyzing specific physician, claim, or patient demographic data that is of medical significance but could have no relevance in another context. Accordingly, summarizer 223 can use the configuration settings to generate both default and custom features as well as features that are based on the specific domain of the data being analyzed.

It is appreciated that many more features than those previously mentioned (e.g., minimum, maximum, average, mean, distribution, etc. . . . ) can be established. Additionally, a single data point or set of data points can produce a significant amount of features. Summarizer 223 can produce many thousands of features based on even simple datasets. In some embodiments the total number of features can be limited to a predefined threshold. In other embodiments, the limit on the number of features included is based only on the physical constraints of the system (e.g., computing device 100) implementing system 200. After features have been established for a particular data set the, established features can be stored in data storage 215, provided directly to analysis engine 230, or provided to booleanizer 224 for additional processing before analysis.

Booleanizer 224 can process the determined features from summarizer 223 and establish corresponding boolean or binary data for those features Using a binary representation of the features can allow the data set to be analyzed using statistical analysis techniques optimized for binary data. Booleanized data can be stored in a data structure similar to data structure 500 of FIG. 5.

Figure 5:
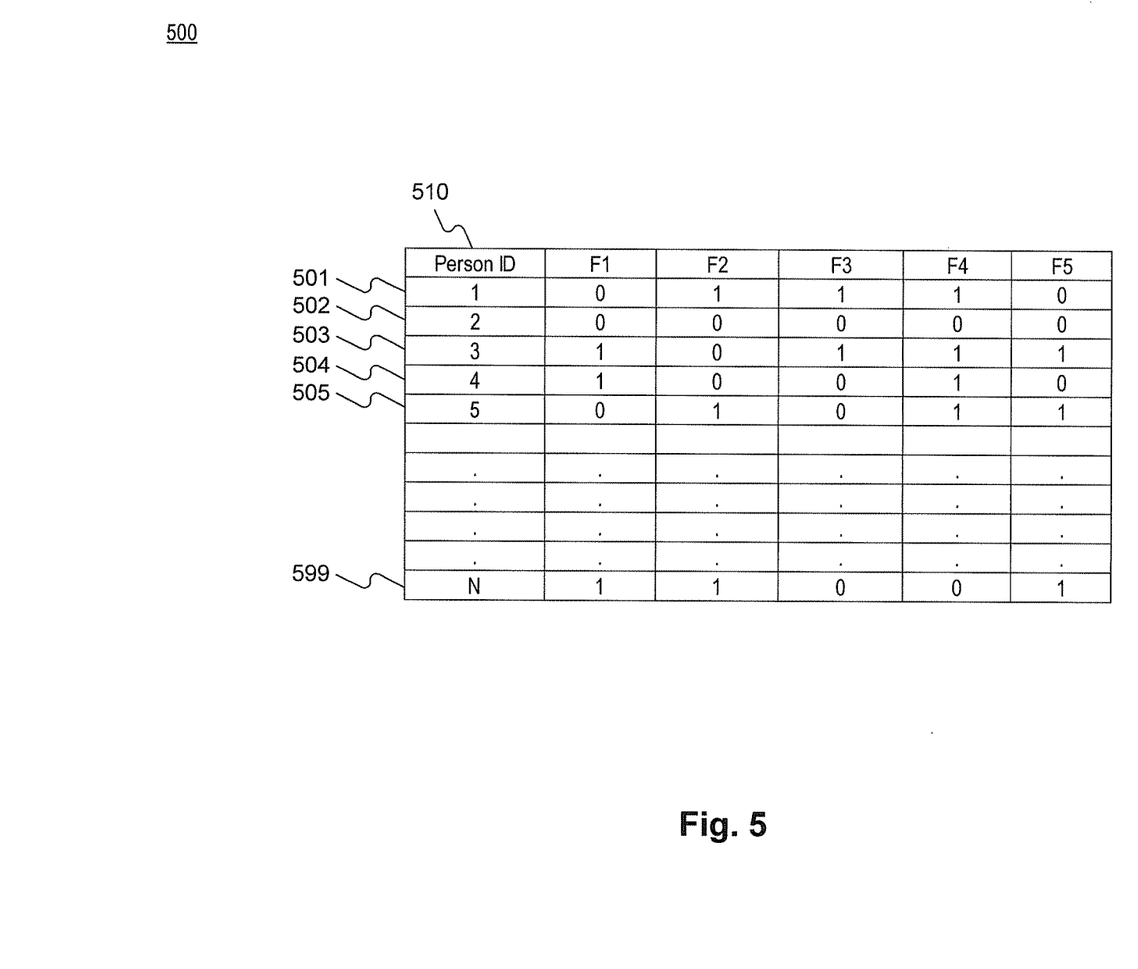
FIG. 5 is an exemplary data structure consistent with embodiments of the present disclosure.

As shown in relation to FIG. 5, booleanizer 224 can produce boolean or binary values based on whether or not a specific feature or attributes exists. For example, a feature of the data that establishes whether or not a particular type of claim exists for a user can easily be represented by a "1" for "True" and a "0" for "False." In this example, the feature can be whether or not an individual has been treated for chest pain. Any individuals who have a claim related to chest pain can be represented with a "1" and the remaining individuals can be represented with a "0" for the category associated with that feature.

As shown in FIG. 5 data structure 500, is an exemplary data structure, consistent with embodiments of the present disclosure. Data structure 500 can use a binary representation of features related to individuals identified by summarizer 223. Similarly to data structure 300 described in FIG. 3 and data structure 400 in FIG. 4, data structure 500 can, for example, be a database, a flat file, data stored in memory (e.g., system memory 121 of computing device 100), an RDBMS, an NRDBMS, and/or data stored in any other suitable storage mechanism (e.g., storage 128 of computing device 100). Moreover, data structure 500 can be implemented or stored on a system similar computing device 100 as described in FIG. 1.

Data structure 500 can store feature information related to individuals. Data structure 500 can include data records 501-505 representing individuals in addition to countless additional records represented by records up to record 599. Data structure 500 can contain many millions or billions of records of data and is limited only by the physical constraints of the system upon which the data structure exists. Moreover, data structure 500 can include many thousands of feature categories in addition to feature categories F1, F2, F3, F4, and F5.

Similarly to data structure 400 in FIG. 4, person ID 510 of FIG. 5 can be a reference to data structure 300 of FIG. 3. Accordingly data record 501 can represent data about the same individual as data record 301 of data structure 300 based on the person ID of each respective data structure. Moreover, as will be demonstrated below, values associated with feature categories F1-F5 can be based on data contained in additional data structures such as data structure 400. Thus, data structures 300, 400, and 500 of FIGS. 3, 4, and 5, respectively, can all be linked based on the person ID categories 310, 420, and 510, respectively. Moreover, each feature category F1-F5 can correspond directly to features identified and/or calculated by summarizer 223.

Once a feature is established and/or calculated as described above (e.g., by summarizer 223) the feature can be processed into a binary value and stored in data structure 500. Data records 501-506 can include this binary data associated with each feature category. For example, data record 501 includes a "0" value for F1 and F5 and a "1" value for F2, F3, and F4. A zero value for a feature category can indicate that the individual referenced by person ID 510 for the data record does not have that particular feature while a one value for a feature category can indicate that the individual referenced by person ID 510 does have that feature.

For example, F1 can represent a feature of "Female." As shown above, person ID 510 can be a reference to additional data structures such as data structure 300 described in FIG. 3. Data records 303 and 304 of data structure 300 include a value of "F" for gender 320. Accordingly, because data records 503 and 504 can refer to data records 303 and 304 based on having the same value for person IDs 310 and 510, data records 503 and 504 can contain a "1" value for the feature of "Female." In this example, because an individual can only be male or female, data records 501, 502, and 505 represent individuals who are male based on the zero value for F1.

In another example, F2 can be a feature representing "Individuals having 2 or more claims." Because data structure 500 can be associated with data structure 400 based on the values of person ID 510 and 420, data structure 400 can be used to populate values for F2 of data structure 500. As shown in FIG. 4, data records 401-403 are associated with individual "1" and data records 405 and 406 are associated with individual "5." Because the data records of data structure 400 can represent individual claims, the data within data structure 400 can be used to populate features related to claims data of data structure 500 in FIG. 5. Data records 501, 503, and 505 can refer to individuals in person ID 510 that also have records in data structure 400 as identified by the same value in person ID 420. Because data structure 400 includes two or more data records for individuals with a person ID of "1" and "5," data records 501 and 505, which can refer to those individuals, can be populated with a "1" value for F2 to indicate that they contain the feature of "Individuals having 2 or more claims."

As another example, a maximum cost feature can be further processed into binary values and stored as part of data structure 500 of FIG. 5. For example, feature category F3 can represent "Individuals who have a maximum cost of at least $1000." Based on the evaluation of the maximum cost feature calculated from data stored in data structure 400 of FIG. 4, data structure 500 can include a "1" value for data records 501 and 503 which are associated with individuals having an ID of "1" and "3." Similarly, data records 502, 504, and 505 can include a "0" value indicating that the individuals associated with those records had a maximum cost of less than $1000. These examples are only exemplary and any feature can be converted into a binary representation and stored as part of data structure 500. Additional examples are described in reference to booleanizer 224 of FIG. 2.

Referring back to FIG. 2, booleanizer 224 can produce multiple binary features based on one or more specific non-binary features. For example, quantile binning or hashing techniques can be used to classify categorical data. Data that represents a range or duration can be represented by the quantile bin with which that range corresponds.

For example, claim data related to the treatment of chest pain may indicate that different specific individuals are treated for chest pain over different durations of time. In this example, if the range of days of treatment represented in the data set is between 0 and 1000 days, a binary representation of the duration feature can be obtained by splitting the possible range into 4 groups of 250 days each. Further, in this example, each individual's binary representation can include a feature category for each of the four groups with a "1" value for the specific data range that relates to that individual's chest pain duration and a "0" value for all other durations for that individual. For example, an individual who suffered from chest pain for 400 days could have a "0" for feature categories representing duration ranges of 1-250 days, 501-750 days, and 751-1000 days and a "1" value for the feature category representing the duration range of 251-500 days. The number of bins used can be increased or decreased based on the specific data type, the data represented, the specific domain, or other factors. In some embodiments, the same duration data could be processed using multiple bin sets. For example, duration data could be processed using a 4 bin set as well as processed using a 10 bin set. The binary output from both sets of processing can be stored for the individual and included as part of the later analysis.

After processing the data, featurization engine 220 can produce feature data directly from summarizer 223 and/or binary feature data from booleanizer 224. This data can be stored in data storage 215 for later analysis or passed directly to analysis engine 230.

Analysis engine 230 can analyze the features and/or binary data produced by featurization engine 220 to determine which features are most indicative of the occurrence of the target event. Analysis engine 230 can use a variety of methods for analyzing the many thousands, millions, or billions of features that can be produced by featurization engine 220. Examples of analysis techniques include feature subset selection, stepwise regression testing, and/or other regularization methods that encourage sparsity (e.g., coefficient shrinkage).

An additional mechanism for analyzing features produced by featurization engine 220 is chi-squared ($\chi^2$) testing. Analysis engine 230 can run a $\chi^2$ test on each feature provided by featurization engine 220 and produce values that represents the feature's predictive significance for the target event. For example, the $\chi^2$ analysis can take as input binary data structure 500 of FIG. 5 as well as a representation of the target event (e.g., in the form of a binary target vector). The $\chi^2$ test can than analyze the binary features provided in, for example, data structure 500 to determine which of those features are potential predictors of the target event. By analyzing the resulting values, analysis engine 230 can identify a set of features that are most indicative of a target event. Additionally, analysis engine 230 can determine the number of features to use in the model based on the large scale hypothesis testing (e.g., $\chi^2$ testing). The testing can rank features and provide regularization in the final model to choose the number of features to use in the model. The resulting model can later be tested using techniques such as cross validation to optimize the specific number of features that provide the best result.

Moreover, the values resulting from the analysis can be used to limit the number of features used in the model to ensure optimal predictions. Analysis engine 230 can use this output to produce a model for application to existing and future data to identify individuals who will likely experience the target event (e.g., a heart attack).

Analysis engine 230 can store the created data model in data storage 215 for future use. Additionally, the data model can be provided to feedback engine 240 for refinement. Feedback engine 240 can apply the data model to a wider set of data to determine the accuracy of the model. Based on those results, feedback engine 240 can report results back to featurization engine 220 to iteratively update the specific inputs used by annotator 221, data censor 222, and summarizer 223 to adjust the model. In this way, featurization engine 220 can be trained as more and more data is analyzed.

In some embodiments, feedback engine 240 includes providing the model to domain experts. The domain experts can evaluate the model and, based on their experience, suggest additional changes to the inputs used by the various components of featurization engine 220. For example, a healthcare model can be provided to physicians to ensure the identified features are consistent with published literature and standard practice. Accordingly, system 200 can iteratively improve the data model for more accurate results.

In some embodiments, feedback engine 240 can use a variety of statistical analysis techniques to test the accuracy and usefulness of a specific model or of multiple models generated for a target event. The models can be evaluated using evaluation metrics such as, among others, precision, recall, accuracy, area under the receiver operator characteristic (ROC) curve, the area under the precision recall (PR) Curve, lift, and/or precision at rank. Feedback engine 240 can provide feedback that is intended to optimize the model based on the specific domain and use case for the model. For example, in a healthcare context, if the model is being used to identify individuals who could need surgery, feedback engine 240 can provide feedback and adjustments to featurization engine 220 to optimize the model for high recall with the understanding that false positives could lead to an innocuous physician visit but false negatives could result in missing individuals who need surgical intervention. In other contexts, such as determining the quality of a service, feedback engine 220 can optimize for high precision in order to ensure accuracy by minimizing false positives at the expense of failing to identify some services or service providers. Additionally, as previously described, feedback engine 240 can test the model using techniques such as cross validation in order to optimize for the number of features chosen for the model by analysis engine 230.

System 200 can further include user interface 250. User interface 250 can be a graphical user interface (GUI) implemented on a computing device such as computing device 100 of FIG. 1 utilizing graphic memory 126, GPU(S) 125, and display device 124. User interface 250 can provide a representation of the data from featurization engine 220, analysis engine 230 and/or feedback engine 240. User interface 250 can be a read-only interface that does not accept user input. In some embodiments, user interface 250 can accept user input to control the representation. In other embodiments, user interface 250 can accept user input to control or modify the components of system 200. User interface 250 can be text based or can include graphical components that represent the displayed data.

In some embodiments user interface 250 can be provided to a user in order to make recommendations based on the predictive model generated by system 200. For example, system 200 can be used to generate a predictive model for heart attacks. The results of this model can be presented to patients whose past medical data can indicate that they are at risk for a heart attack. The individual users will have no insight into the specific data model, itself, but will benefit from the ability to seek preventive care based on their past history.

In some embodiments, user interface 250 can provide a representation of the functioning of featurization engine 220, analysis engine 230, and/or feedback engine 240. This representation can include components such as the inputs to system 200, the outputs from each component in system 200 (e.g., annotator 221, data censor 222, summarizer 223, booleanizer 224, and or analysis engine 230). This information can be used to further understand the relationship between certain identified features and the prediction model generated by the system. In some embodiments, user interface 250 further accepts user input to control or modifying settings or configurations for the various components of system 200.

In some embodiments, user interface 250 can display feedback information from feedback engine 240. In these embodiments, domain experts can use user interface 250 to verify the generated models, provide feedback regarding the generated models, and or modify the inputs or data used by featurization 220 to generate the models.

System 200 can be used as described to quickly and accurately produce effective predictive models across many different domains. Instead of requiring labor and time intensive methods for generating narrow predictive models, system 200 can be used to quickly generate and iterate on predictive models that are generic enough to be applied to wide ranges of future data while at the same time utilize statistically significant features to best predict a target event.

Figure 6:
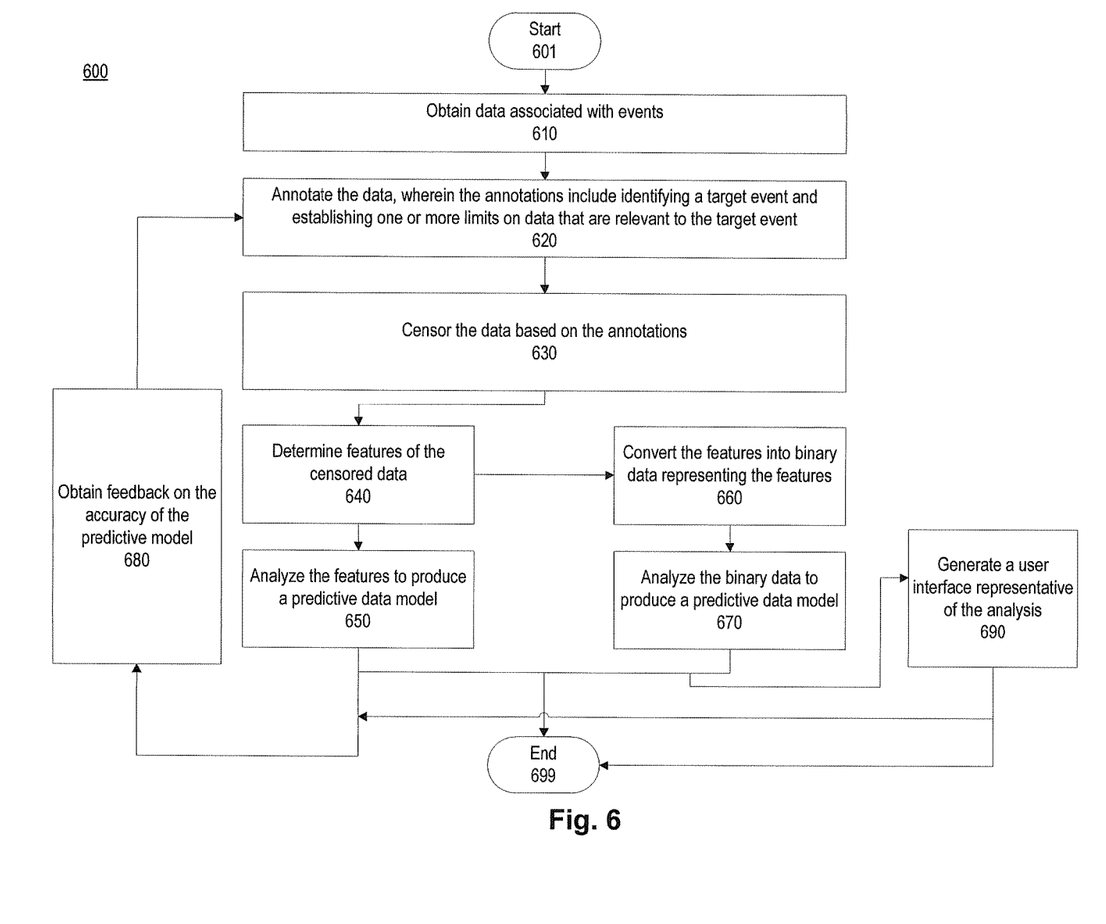
FIG. 6 is a flowchart of an exemplary method for data driven featurization, consistent with embodiments of the present disclosure.

FIG. 6 is a flowchart of an exemplary method 600 for data driven featurization. It will be readily appreciated that the illustrated procedure can be altered to delete steps or further include additional steps. After initial step 600, the system (e.g., system 200 from FIG. 2) can obtain (step 610) data associated with at least one event (e.g., data stored in data structure 400 of FIG. 4). Obtaining the data can include, as described in relation to FIG. 2, extracting (e.g., using data extractor 211) the data from multiple data sources (e.g., data sources 201-204), transforming the data (e.g, using data transformer 212), and loading the data (e.g., using data loader 213) into a storage location (e.g., data storage 215) for additional analysis. Through this process, the system can prepare data from a variety of sources into a normalized and consistent representation ready for further processing.

The system can further annotate (step 620) the data (e.g., using annotator 221 as shown in FIG. 2). The system can both identify a target event (e.g., one of the data records in data structure 400 of FIG. 4) and establish one or more limits on the data relevant to the target event. For example, the system can establish an end date and beginning date related to a particular target event.

After annotation, the system can censor (step 630) the data (e.g., using data censor 222) based on the annotations. Censoring the data can include using the annotations to remove data from the dataset that falls outside the annotated limits on the data. The system can censor the data resulting in a dataset that includes data relevant to the target event while also reducing the possibility of including data that might not be relevant when the model is applied to future data. The system can censor data to improve the predictive accuracy of the model when applied to future data sets. Censoring the data can be important as it helps to avoid overfitting and look-ahead bias.

After censoring the data, the system can determine (step 640) features of the censored data (e.g., using summarizer 223). As described in relation to system 200 of FIG. 2 and data structure 500 of FIG. 5, features can be descriptive of the data being analyzed. In the case of real numbers, features can include a maximum, minimum, average, mean, and other statistical characteristics or values associated with a number from a single data record or numbers across multiple data records. Additionally, features can include categorization information such as, in the example of claim data (e.g., the data stored in data structure 400 of FIG. 4), the most frequent claims, most expensive claims, number of claims, and/or codes identifying the claims. Features related to dates can include duration. Further, the system can utilize external data (e.g., data stored in data storage 215 of FIG. 2) associated with data structures 200 or 300 of FIGS. 2 and 3, but not stored as part of those data structures, to further generate features. As previously described, the listed features are not exhaustive and other features can be calculated, determined, and/or used. Moreover, a single data point or group of data points can result in many more features associated with the data. Accordingly, many thousands of features can be established for a data set. After features are determined the system can analyze (step 650) the features or, optionally, booleanize (step 660) the features.

The system can analyze (step 650) the features (e.g., using analysis engine 230 of FIG. 2). This analysis can use various statistical analysis techniques in order to determine which of the determined features are most relevant to predicting the target event. For example, the system can utilize $\chi^2$ testing to determine features most relevant to predicting the target event. As explained above, this analysis can be based on specific characteristics of the domain and the data being analyzed. The system can produce a predictive model based on the statistical analysis.

Optionally, the system can booleanize (step 660) the features into a binary or boolean data (e.g., using booleanizer 224). As previously described in relation to FIG. 2, converting the feature data into a binary representation can include storing a binary value to indicate whether or not an individual is associated with a specific feature. Moreover, as explained above, features that include categories of data can be analyzed using techniques such as quantile binning where each bin is represented by a separate feature and an individual has a binary "1" value for bin associated with the specific individual.

After converting the features into binary data, the system can analyze (step 670) the binary data using various statistical analysis techniques (e.g. using data analysis engine 230 of FIG. 2). By converting the data into a binary representation of features, the system can utilize a larger variety of statistical analysis techniques. From analysis of either the binary or non-binary features, the system can produce a predictive model.

After a predictive model is created, the system can obtain (step 680) feedback on the accuracy of the predictive model (e.g., using feedback engine 240 of FIG. 2). The system can analyze the accuracy of the generated model by applying the predictive model to a larger data set and analyzing the results directly or by soliciting feedback from domain experts on whether the features identified in the model are accurate or relevant predictors for the event. Based on the feedback, the system can return to the annotation process (step 620) to refine the model based on the feedback.

Additionally, after the predictive model is created the system can generate (step 690) a user interface representative of the analysis. The user interface can include data related to the various components (e.g., annotator 221, data censor 222, summarizer 223, booleanizer 224, analysis engine 230, and feedback engine 240 of FIG. 2). The user interface can also include data related to the predictive model generated by system 200. In some embodiments, the user interface can accept user input for controlling or modifying the interface and/or the various components of the system. The user interface can also be used to provide feedback obtained (e.g., at step 680) by the system.

In the foregoing specification, embodiments have been described with reference to numerous specific details that can vary from implementation to implementation. Certain adaptations and modifications of the described embodiments can be made. Other embodiments can be apparent to those skilled in the art from consideration of the specification and practice of the invention disclosed herein. It is intended that the specification and examples be considered as exemplary only. It is also intended that the sequence of steps shown in figures are only for illustrative purposes and are not intended to be limited to any particular sequence of steps. As such, those skilled in the art can appreciate that these steps can be performed in a different order while implementing the same method.

What is claimed is:

1. An electronic device for producing predictive models comprising:

a data storage configured to store one or more data sets associated with a target event, wherein the target event is associated with a healthcare condition;

a data input engine configured to obtain the one or more data sets associated with the target event from one or more data sources, wherein at least one of the one or more data sources is associated with healthcare information;

a featurization engine comprising:
 an annotator configured to annotate the one or more data sets, wherein the annotations include an identification of the target event, an identification of records of the one or more data sets that are associated with the target event, and an establishment of one or more limits on the one or more data sets based on established criteria;
 a data censor configured to censor the one or more data sets based on the annotations, wherein censoring the data includes filtering from the one or more data sets records that do not meet the established criteria; and
 a summarizer configured to determine one or more features of the censored data, wherein the one or more features are representative of data in the one or more data sets and wherein at least one of the one or more features is based on a domain of the target event;

an analysis engine configured to:
 analyze the one or more features, wherein the analysis identifies a subset of the one or more features that are indicative of the target event; and
 produce a predictive model based on the analysis, wherein the predictive model provides an indication of a future occurrence of the target event based on data associated with a person.

2. The electronic device of claim 1, wherein the featurization engine is further configured to convert the features into a binary representation of the features and the analysis engine is further configured to analyze the binary representation.

3. The electronic device of claim 2, wherein conversion of features into the binary representation uses quantile binning.

4. The electronic device of claim 2, wherein the analysis of the binary representation includes chi-squared modeling.

5. The electronic device of claim 1, further comprising a feedback engine configured to obtain feedback associated with the predictive model.

6. The electronic device of claim 5, wherein the feedback engine obtains feedback from domain experts.

7. A method performed by one or more processors for producing predictive models and comprising:

obtaining one or more data sets associated with a target event from one or more data sources, wherein the target event is associated with a healthcare condition and wherein at least one of the one or more data sources is associated with healthcare information;

annotating the one or more data sets, wherein the annotations include identifying the target event within the one or more data sets, identifying records of the one or more data sets that are associated with the target event, and establishing one or more limits on the one or more data sets based on established criteria;

censoring the one or more data sets based on the annotations, wherein censoring the data includes filtering from the one or more data sets records that do not meet the established criteria;

determining one or more features of the censored data, wherein the one or more features are representative of data in the one or more data sets and wherein at least one of the one or more features is based on a domain of the target event;

analyzing the one or more features, wherein the analysis identifies a subset of the one or more features that are indicative of the target event; and producing a predictive model based on the analysis, wherein the predictive model provides an indication of a future occurrence of the target event based on data associated with a person.

8. The method of claim 7, further comprising converting the one or more features into a binary representation and analyzing the binary representation.

9. The method of claim 8, wherein converting the one or more features into a binary representation uses quantile binning.

10. The method of claim 8, wherein analyzing the binary representation uses chi-squared modeling.

11. The method of claim 7, further comprising obtaining feedback associated with the predictive model.

12. The method of claim 11, wherein the feedback is obtained from domain experts.

13. A non-transitory computer readable storage medium storing a set of instructions that are executable by a first computing device that includes one or more processors to cause the first computing device to perform a method for producing predictive models, the method comprising:

obtaining one or more data sets associated with a target event from one or more data sources, wherein the target event is associated with a healthcare condition and wherein at least one of the one or more data sources is associated with healthcare information;

annotating the one or more data sets, wherein the annotations include identifying the target event within the one or more data sets, identifying records of the one or more data sets that are associated with the target event, and establishing one or more limits on the one or more data sets based on established criteria;

censoring the one or more data sets based on the annotations, wherein censoring the data includes filtering from the one or more data sets records that do not meet the established criteria;

determining one or more features of the censored data, wherein the one or more features are representative of data in the one or more data sets and wherein at least one of the one or more features is based on a domain of the target event;

analyzing the one or more features, wherein the analysis identifies a subset of the one or more features that are indicative of the target event; and producing a predictive model based on the analysis, wherein the predictive model provides an indication of a future occurrence of the target event based on data associated with a person.

14. The non-transitory computer-readable storage medium of claim 13, wherein the set of instructions that are executable by the one or more processors of the first computing device cause the first computing device to further perform:

converting the one or more features into a binary representation and analyzing the binary representation.

15. The non-transitory computer-readable storage medium of claim 14, wherein converting the one or more features into a binary representation uses quantile binning.

16. The non-transitory computer-readable storage medium of claim 14, wherein analyzing the binary representation uses chi-squared modeling.

17. The non-transitory computer-readable storage medium of claim 13, wherein the set of instructions that are executable by the one or more processors of the first computing device cause the first computing device to further perform:

obtaining feedback associated with the predictive model.

18. The non-transitory computer-readable storage medium of claim 17, wherein the feedback is obtained from domain experts.

* * * * *

UNITED STATES PATENT AND TRADEMARK OFFICE
CERTIFICATE OF CORRECTION

| | | |
|---|---|---|
| PATENT NO. | : 10,430,716 B2 | Page 1 of 1 |
| APPLICATION NO. | : 15/040963 | |
| DATED | : October 1, 2019 | |
| INVENTOR(S) | : Seiji James Yamamoto | |

It is certified that error appears in the above-identified patent and that said Letters Patent is hereby corrected as shown below:

On the Title Page

(73) Assignee: "GROUND ROUNDS, INC.", should read -- GRAND ROUNDS, INC. --.

Signed and Sealed this
Seventh Day of April, 2020

Andrei Iancu
*Director of the United States Patent and Trademark Office*